United States Patent
Sjoberg

(10) Patent No.: US 7,785,620 B1
(45) Date of Patent: Aug. 31, 2010

(54) CHOLESTEROL LOWERING AND BLOOD LIPIDS LOWERING COMPOSITION

(75) Inventor: Kjell Sjoberg, Danderyd (SE)

(73) Assignee: Triple Crown AB, Stockholm (SE)

( * ) Notice: Subject to any disclaimer, the term of this patent is extended or adjusted under 35 U.S.C. 154(b) by 1379 days.

(21) Appl. No.: 10/111,614

(22) PCT Filed: Oct. 27, 2000

(86) PCT No.: PCT/SE00/02100

§ 371 (c)(1),
(2), (4) Date: Dec. 2, 2002

(87) PCT Pub. No.: WO01/30359

PCT Pub. Date: May 3, 2001

(30) Foreign Application Priority Data

Oct. 29, 1999 (SE) .................................... 9903915

(51) Int. Cl.
*A61K 47/36* (2006.01)
*A61K 47/44* (2006.01)

(52) U.S. Cl. ..................................... 424/439

(58) Field of Classification Search ........................ None
See application file for complete search history.

(56) References Cited

U.S. PATENT DOCUMENTS

| | | | |
|---|---|---|---|
| 4,218,334 A | | 8/1980 | Lundmark |
| 4,996,063 A | * | 2/1991 | Inglett .......................... 426/21 |
| 5,502,045 A | * | 3/1996 | Miettinen et al. ............ 514/182 |
| 5,792,754 A | * | 8/1998 | Green et al. ................... 514/60 |
| 5,883,273 A | * | 3/1999 | Miller et al. .................. 554/169 |
| 6,149,961 A | * | 11/2000 | Kepplinger et al. .......... 426/553 |

FOREIGN PATENT DOCUMENTS

| | | | |
|---|---|---|---|
| EP | 0898896 A1 | | 3/1999 |
| EP | 0 990 391 | * | 4/2000 |
| EP | 0990391 A1 | | 4/2000 |
| EP | 1197153 A1 | | 4/2002 |
| GB | 1365661 | | 9/1974 |
| JP | 61015647 A2 | | 1/1986 |
| WO | 9219640 A1 | | 11/1992 |
| WO | WO-94/20072 | | 9/1994 |
| WO | 9915546 A1 | | 4/1999 |
| WO | 9925362 A1 | | 5/1999 |

OTHER PUBLICATIONS

Inglett et al, "Oat Beta-Glucan-Amylodextrins: Preliminary Preparations and Biological Properties", Plant Foods for Human Nutrition, vol. 45, No. 1, pp. 53-61, Jan. 1994, Abstract only.*
Brufau et al, Phytosterols and pectin added to a high staurated fat diet do not show hypocholesterolemic effect in female guinea pigs, European Journal of Lipid Science and Tecnology, vol. 110, pp. 206-215, February 20, 2008.*
Inglett, Chemtech, pp. 38-42 (1999).
Gylling et al., Scandanavan Journal of Nutrition, vol. 44, pp. 155-157 (2000).
STN International, File CA, Chemical Abstracts, vol. 104, No. 19, May 12, 1996.
O. J. Pollak, "Effect of Plant Sterols on Serum Lipids and Atherosclerosis," Pharmac. Ther., vol. 31, pp. 177-208, 1985.

* cited by examiner

*Primary Examiner*—Carlos A Azpuru
(74) *Attorney, Agent, or Firm*—Birch, Stewart, Kolasch & Birch, LLP

(57) ABSTRACT

The present invention is a composition containing cholesterol lowering and blood lipids lowering components such as phytosterols in a biologically easily available form in combination with unsaturated fatty acids or esters, short chain fatty acids or esters and/or hydrolyzed flour containing β-glucan and amylodextrin; food containing such a composition and a method for manufacturing of such a composition.

20 Claims, No Drawings

CHOLESTEROL LOWERING AND BLOOD LIPIDS LOWERING COMPOSITION

This application is the national phase under 35 U.S.C. §371 of PCT International Application No. PCT/SE00/02100 which has an International filing date of Oct. 27, 2000, which designated the United States of America.

BACKGROUND

Phytosterols such as β-sitosterol and β-sitostanol and their derivatives are used in medicine owing to their ability to lower total and LDL-cholesterol levels in blood. Recent research has shown that n-3 polyunsaturated fatty acids present in fish oils such as eicosapentaenic acids (EPA) and docosahexaenic acids (DHA) positively effect our blood lipids (1). They are also building blocks in prostaglandins. Further a positive effect on blood lipids has been noted by intake of shorter fatty acids (2). Finally, the importance of a daily intake of β-glucan and amylodextrins is recommended by USDA. (3,4). These compounds can be recovered by hydrolysis of oat meal and can be made in gelform as hydrocolloids.

Disclosed is a composition containing cholesterol lowering and blood lipids lowering components in which phytosterols, mixed with esters of unsaturated fatty acids and/or esters of short chain fatty acids, are distributed in monomolecular, low associated or cluster form in hydrolysed fibres containing β-glycan and amylodextrines.

In one embodiment, the cholesterol lowering component contains β-sitosterol and/or β-sitostanol.

In another embodiment, the cholesterol lowering component contains β-sitosterol esters and/or β-sitostanol esters of polyunsaturated fatty acids.

In another embodiment, the cholesterol lowering component contains β-sitosterol esters and/or β-sitostanol esters of short chain fatty acids.

In another embodiment, the blood lipids lowering component contains fish oil and/or mono and diglycerides of polyunsaturated fatty acids.

In another embodiment, the blood lipids lowering component contains tri- and/or mono- and diglycerides of short chain fatty acids.

In another embodiment, the blood lipids lowering component contains a mixture of fish oil and triglycerides of short chain fatty acids.

In another embodiment, the blood lipids lowering and stabilising component contains hydrolysed meal containing a soluble fibre such as β-glycan or amylodextrins.

Also disclosed is a method to prepare the present composition in which fish oil and/or triglycerides of short chain fatty acids are mixed with glycerol and phytosterols, transesterfied at elevated temperatures at 130-230° C. and that the mixture obtained is spread and stabilized in a gel based on hydrolyzed fibers.

Further disclosed is food containing the present composition in a suitable amount for a cholesterol and blood lipids lowering effect.

Also disclosed is a capsule or tablet containing the present composition.

DESCRIPTION OF THE INVENTION

In the present invention is shown how sterols and/or stanols in a biologically easily available form has successfully been combined with other blood lipids lowering and cholesterol lowering compounds such as unsaturated fatty acids or their derivatives and/or shorter fatty acids or derivatives of these and/or soluble fibers including β-glucan or amylodextrines. Soluble fibers may be obtained from the hydrolysis of meal. A clear distinction between blood lipids lowering and cholesterol lowering action of these compound is not present, furthermore interactive effects may occur.

Sterols and/or stanols are initially mixed with an oil such as fish oil and esters of shorter fatty acids and glycerol. The mixture is transesterified in a known manner to mainly monoglycerides of fatty acids from fish oil or shorter fatty acids. In this way we obtain in only one process step an entirely new combination of cholesterol lowering sterols and or stanols and good fatty acids in a concentrate, in some cases in the same molecule. The concentrate can be used such, be tabletted, encapsulated or mixed with food. The concentrate can also be mixed with hydrolysed fibres in gel- or powder form. The obtained mixture contains all desired components for blood lipids lowering and cholesterol lowering effects. The obtained mixture can be mixed into food such as bread, cakes, flakes and other or be encapsulated or tabletted. The advantrages besides the pure biological are that the oxygene sensitive polyunsaturated fatty acids are stabilsed by the hydrolysed meal. The manufacturing process is simple and cheap. For different applications one or more of the components can be excluded. The present invention will be described below by non limiting examples.

EXAMPLE 1

55 g of fishoil, 25 g of short chain fatty acids, 18 g of glycerol and 40 g of sterols are mixed in a vessel under inert athmosphere and are transesterified at elevated temperatures between 130-230° C. in a known way. After cooling to 50-80° C. the mixture is added to 400 g of a gel based on hydrolysed meal under good stirring. If desired stabilizers for unsaturated fatty acids can be added and/or the mixture can be kept under inert athmosphere.

The obtained composition can be used as is or be mixed into various food.

EXAMPLE 2

50 g of oil containing polyunsaturated fatty acids, 25 g of oils from short chain fatty acids, 18 g of glycerol and 40 g of sterols are mixed in a vessel under inert athmosphere and are transesterified at elevated temperatures in known way. After cooling to 50-80° C. the mixture is added to 2500 g of a gel based on hydrolysed oats fibre under good stirring.

The obtained composition can be used as is or be mixed into into various food.

EXAMPLE 3

55 g of an oil containing polyunsaturated fatty acids, 10 g of glycerol and 40 g of sterols are transesterified in known way as in example 1. Alter cooling to 50-80° C. the mixture is added to 400 g of a gel based on hydrolysed oats fibre under good stirring.

The obtained composition can be used as is or mixed into various food.

EXAMPLE 4

500 g of fish oil, 100 g of oil of short chain fatty acids, 150 g of glycerol and 300 g of sterols transesterified as in ex 1. The composition obtained can be used as such or mixed into different food, be encapsulated or tabletted.

EXAMPLE 5

65 g of oils of short chain fatty acids, 18 g of glycerol and 40 g of sterols are mixed in a vessel under inert athmosphere and transesterified at elevated temperature in known way. After cooling to 50-80° C. the mixture is added under good stirring to 400 g of gel based on hydrolysed oats fibre. The obtained composition can be used as is, be encapsulated, tabletted or mixed into different food.

EXAMPLE 6

40 g of sterols are dissolved in 50 g of fish oil and 40 g of a monoglyceride in a vessel under inert athmosphere at 100° C. The composition obtained can be used as is, be encapsulated, tabletted or mixed into different food.

EXAMPLE 7

50 g of sterols are mixed with 65 g of oils of short chain fatty acids and 15 g of glycerol and the mixture is transesterified as in ex 1. The obtained composition can be used as is, be encapsulated, tabletted or mixed into different food.

EXAMPLE 8

20 g of sterols are dissolved in 40 g of monoglycerides at 85° C. and added to 200 g of gelbased hydrolysed oats fibre under good stirring. The composition obtained can be used as is, been capsulated, tabletted or mixed into various food.

The invention claimed is:
1. A composition comprising:
   (1) phytosterols;
   (2) at least one blood lipids lowering component comprising fish oil; and
   (3) soluble fibers,
   wherein
      (a) at least a part of said phytosterols is esterified with at least a part of fatty acids of said at least one blood lipids lowering component comprising fish oil,
      (b) at least a part of said blood lipids lowering component comprises fish oil and one or more component chosen from mono- and di-glycerides of fish oil,
      (c) said esters of (a) are distributed in said soluble fibers, and
      (d) said phytosterols and said at least one blood lipids lowering component are present in a suitable amount for a cholesterol and blood lipids lowering effect.
2. The composition as in claim 1, wherein said phytosterols comprise β-sitosterol and/or β-sitostanol.
3. The composition as in claim 1, wherein said phytosterols esterified with said at least one blood lipids lowering component comprises β-sitosterol esters and/or β-sitostanol esters of polyunsaturated fatty acids, wherein said fatty acids originate from fish oil.
4. The composition as in claim 1, wherein at least a part of said at least one blood lipids lowering component comprises fish oil and/or mono and diglycerides of polyunsaturated fatty acids.
5. The composition as in claim 1, wherein said soluble fibers are obtained by hydrolysis of meal.
6. A method for preparing the composition as in claim 1, comprising:
   mixing fish oil with glycerol and phytosterols;
   esterifying the mixture; and
   stabilizing the obtained mixture in a gel based on soluble fibers.
7. Food comprising the composition as in claim 1 in a suitable amount for a cholesterol and blood lipids lowering effect.
8. A capsule or tablet comprising the composition as in claim 1.
9. The composition as claimed in claim 1, wherein the at least one blood lipids lowering component comprises monoglycerides of fatty acids from fish oil and/or polyunsaturated fatty acids.
10. A method for preparing the composition as in claim 1, comprising:
    esterifying a mixture of phytosterols, glycerol and fish oil; and
    stabilizing the obtained product in soluble fibers containing β-glucans and/or amylodextrins.
11. The composition as in claim 1, wherein said soluble fibers comprise β-glucan and/or amylodextrins.
12. The method as in claim 6, wherein said esterifying is carried out at a temperature of 130° C.-230° C.
13. A composition comprising:
    (1) phytosterols comprising β-sitosterol and/or β-sitostanol;
    (2) a blood lipids lowering component comprising fish oil; and
    (3) soluble fibers,
    wherein
       (a) said phytosterols are esterified with said blood lipids lowering component to form β-sitosterol esters and/or β-sitostanol esters of polyunsaturated fatty acids from fish oil,
       (b) said blood lipids lowering component comprises fish oil and one or more component chosen from (1) monoglycerides of polyunsaturated fatty acids, and (2) diglycerides of polyunsaturated fatty acids,
       (c) said esters of (a) are distributed in said soluble fibers, and
       (d) said phytosterols and said blood lipids lowering component are present in a suitable amount for a cholesterol and blood lipids lowering effect.
14. The composition as in claim 13, wherein said blood lipids lowering component comprises fish oil and mono and diglycerides of polyunsaturated fatty acids.
15. The composition as in claim 13, wherein said soluble fibers are obtained by hydrolysis of meal.
16. The composition as in claim 13, wherein said soluble fibers comprise β-glucans and/or amylodextrins.
17. A composition comprising:
    (1) phytosterols;
    (2) at least one blood lipids lowering component; and
    (3) soluble fibers,
    wherein
       (a) at least a part of said phytosterols is esterified with at least a part of fatty acids of said at least one blood lipids lowering component,
       (b) at least a part of said blood lipids lowering component comprises fish oil and monoglycerides of fish oil,
       (c) said esters of (a) are distributed in said soluble fibers, and
       (d) said phytosterols and said at least one blood lipids lowering component are present in a suitable amount for a cholesterol and blood lipids lowering effect.
18. A composition comprising:
    (1) phytosterols comprising β-sitosterol and/or β-sitostanol;

(2) a blood lipids lowering component; and
(3) soluble fibers,
wherein
- (a) said phytosterols are esterified with said blood lipids lowering component to form β-sitosterol esters and/or β-sitostanol esters of polyunsaturated fatty acids from fish oil,
- (b) said blood lipids lowering component comprises fish oil and monoglycerides of fish oil,
- (c) said esters of (a) are distributed in said soluble fibers, and
- (d) said phytosterols and said blood lipids lowering component are present in a suitable amount for a cholesterol and blood lipids lowering effect.

19. A composition comprising:
(1) phytosterols;
(2) at least one blood lipids lowering component comprising fish oil; and
(3) soluble fibers,
wherein
- (a) at least a part of said phytosterols is esterified with at least a part of fatty acids of said at least one blood lipids lowering component comprising fish oil,
- (b) at least a part of said blood lipids lowering component comprises fish oil and one or more component chosen from mono- and di-glycerides of polyunsaturated fatty acids,
- (c) said esters of (a) are distributed in said soluble fibers, and
- (d) said phytosterols and said at least one blood lipids lowering component are present in a suitable amount for a cholesterol and blood lipids lowering effect.

20. A composition comprising:
(1) phytosterols comprising β-sitosterol and/or β-sitostanol;
(2) a blood lipids lowering component comprising fish oil; and
(3) soluble fibers,
wherein
- (a) said phytosterols are esterified with said blood lipids lowering component to form β-sitosterol esters and/or β-sitostanol esters of polyunsaturated fatty acids,
- (b) said blood lipids lowering component comprises fish oil and one or more component chosen from (1) monoglycerides of polyunsaturated fatty acids, and (2) diglycerides of polyunsaturated fatty acids,
- (c) said esters of (a) are distributed in said soluble fibers, and
- (d) said phytosterols and said blood lipids lowering component are present in a suitable amount for a cholesterol and blood lipids lowering effect.

* * * * *